(12) United States Patent
Scaiano et al.

(10) Patent No.: US 6,741,347 B1
(45) Date of Patent: May 25, 2004

(54) APPARATUS FOR LASER FLASH PHOTOLYSIS

(75) Inventors: Juan C. Scaiano, Gloucester (CA); Gerry Charette, Ottawa (CA); André Simard, Gatineau (CA)

(73) Assignee: University of Ottawa (CA)

( * ) Notice: Subject to any disclaimer, the term of this patent is extended or adjusted under 35 U.S.C. 154(b) by 0 days.

(21) Appl. No.: 09/662,391

(22) Filed: Sep. 14, 2000

(30) Foreign Application Priority Data

Sep. 16, 1999 (GB) ............................................. 9921972

(51) Int. Cl.$^7$ ................................................. G01J 3/427
(52) U.S. Cl. ........................ 356/319; 356/325; 356/318
(58) Field of Search ................................. 356/318, 409, 356/432, 436, 319–322, 325

(56) References Cited

U.S. PATENT DOCUMENTS

| | | |
|---|---|---|
| 3,811,777 A | 5/1974 | Chance |
| 3,901,600 A | 8/1975 | Johnson, Jr et al. |
| 4,023,905 A | 5/1977 | Chance |

FOREIGN PATENT DOCUMENTS

| | | |
|---|---|---|
| SU | 869465 | 10/1996 |

OTHER PUBLICATIONS

Ebbesen, Review of Scientific Instruments, vol. 59, No. 8, p. 1307–1309 (Aug., 1988).*

* cited by examiner

Primary Examiner—Richard A. Rosenberger
Assistant Examiner—Vincent P. Barth
(74) Attorney, Agent, or Firm—Anthony J. Casella; Gerald E. Hespos (57) ABSTRACT

An apparatus for flash photolysis has a light source and an optical fiber for directing light from the light source and through a sample. A laser or other such device is provided for initiating a chemical change within the sample. Additionally, a device is provided for determining the change in absorption of light by the sample during the chemical change.

10 Claims, 11 Drawing Sheets

APPARATUS FOR LASER FLASH PHOTOLYSIS

FIELD OF THE INVENTION

The present invention relates to the field of laser flash photolysis, and in particular, the present invention provides a novel miniaturized laser flash photolysis system, with improved performance over existing laser flash photolysis systems.

Figure 1:
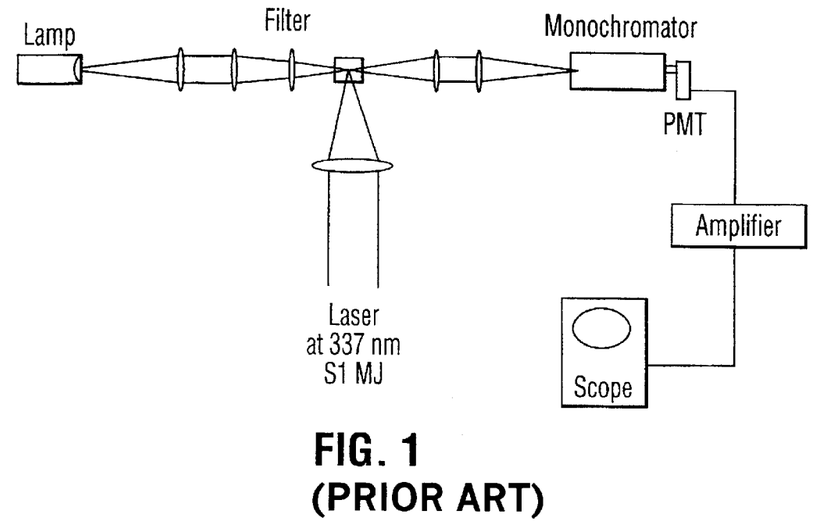
FIG. 1 is a schematic of an early (1960s) layer flash photolysis system.

Laser flash photolysis (LFP) is a technique utilized to study reaction mechanisms in chemical and biological processes. The technique was introduced in 1966 by Lindqvist at the CNRS in France and quickly developed by various research groups around the world. FIG. 1 shows a schematic drawing of this original set up. It can be regarded as a technical development of what is now called "conventional flash photolysis". The development was brought about by the invention of the laser, in the early 1960s.

Figure 2:
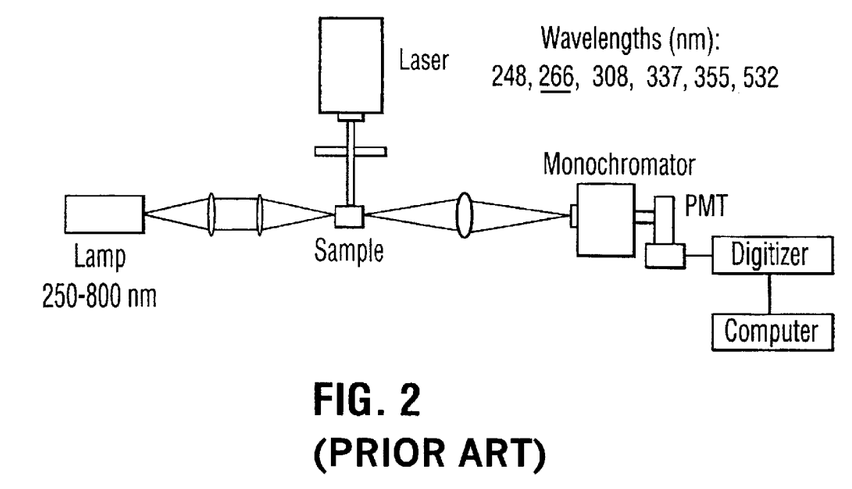
FIG. 2 is a schematic of a conventional prior art laser flash photolysis system.

The technique of LFP, as it has been utilized for the last twenty years (FIG. 2), consists of a pulsed laser source that generates the chemical species to be studied, an optical and electronic system capable of sensing optical changes in the sample, and a computer suitably equipped to capture, process and display the data.

The optical and electronic system mentioned above are the heart of any LFP system. They essentially constitute a fast spectrometer capable of acquiring spectra of very short lived chemical species called "intermediates", and recording their evolution with time, that is, their kinetics. The present invention deals specifically with this part, and can be used with most modem pulsed lasers. Moreover, in order to measure kinetics only, a spectrometer is not required, or the instrument can be used at a fixed wavelength setting.

LFP techniques have evolved over the years to include time resolutions as short as femtosecond ($10^{-15}$ seconds). The invention described here refers to systems with nanosecond resolutions, which usually use lasers with pulse durations between 1 and 20 ns, although the concept is not restricted to this time scale. The detection components of such an LFP system are based on commercial photomultiplier tubes (PMT) and have adequate responses from about 1 nanosecond to macroscopic time scales, although LFP systems are rarely utilized in time scales longer than 1 second.

The term LFP usually refers to the optical and electronic components mentioned above, and practitioners of the technique understand that in addition to the LFP system, a functional instrument also requires a pulsed laser and a computer. Modem LFP systems have a typical footprint of 10 square feet, frequently slightly bigger; this footprint is exclusive of space taken by the laser and the computer. The LFP system is normally mounted on an optical table, or a solid and firm table; such an LFP system is not portable. Transportation normally involves taking apart dozens of components which need to be reassembled, reconnected and properly aligned following any move.

The invention consists of the development of a new miniature laser flash photolysis system (mLFP) which represents a major improvement over existing apparatus. Three aspects of this new mLFP system are important in this regard:

(i) A great reduction in the overall size of the instrument, which has a footprint of less than 2 square feet.

(ii) In contrast with all existing systems, the new set-up is readily portable. It consists of integrated components in an enclosure with a footprint of 12 inches by 18 inches, plus a small digitizer which connects to the enclosure mentioned above and the computer.

(iii) By incorporating an innovative optical design around the sample holder, the new mLFP system does not require "pulsing" the monitoring lamp and is virtually insensitive to scattered light and fluorescence. Scattered light and fluorescence represent major problems in prior LFP methods;

(iv) The instrument lends itself easily to remote sensing, by taking advantage of optical fibers of variable length.

In a broad aspect, then, the present invention relates to an apparatus for flash photolysis including: i) a source of light radiation; ii) optical means for channeling light from said source through a sample; iii) means to initiate a chemical change in said sample; iv) means for measuring the change in absorption of said light radiation by said sample during said chemical change.

BRIEF DESCRIPTION OF THE DRAWINGS

In drawings that illustrate the present invention by way of example.

DETAILED DESCRIPTION

Referring to the drawings, the structural aspects of the laser flash photolysis (LFP) unit of the present invention are illustrated in FIGS. 6, 7, 7A, 8 and 8A. The unit is contained entirely (save for the laser and the computer) in a housing comprising two stacked plates, a base plate on which is mounted the electronics of the unit, the monochrometer and the detector, and a top level plate. The top level plate is divided into two portions; a space for mounting a lamp housing, and a space for mounting a sample holder. The sample holder space is provided with a 'bread board' comprising a grid of drilled, tapped holes into which components can be quickly mounted/demounted. The top and bottom plates are fabricated from a suitably stiff material such as ¼" aluminum plate to ensure the structural rigidity of the unit when assemble.

Figure 5:
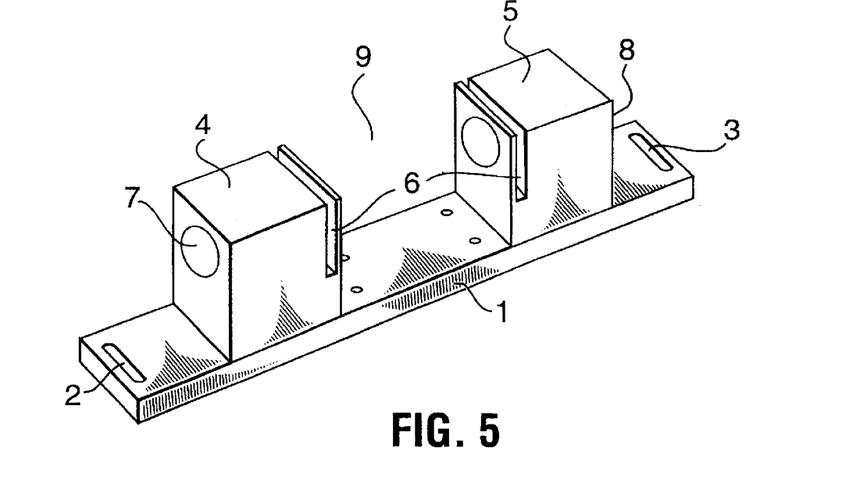
FIG. 5 is a perspective view of a sample holder block for use in the present invention.
Figure 5A:
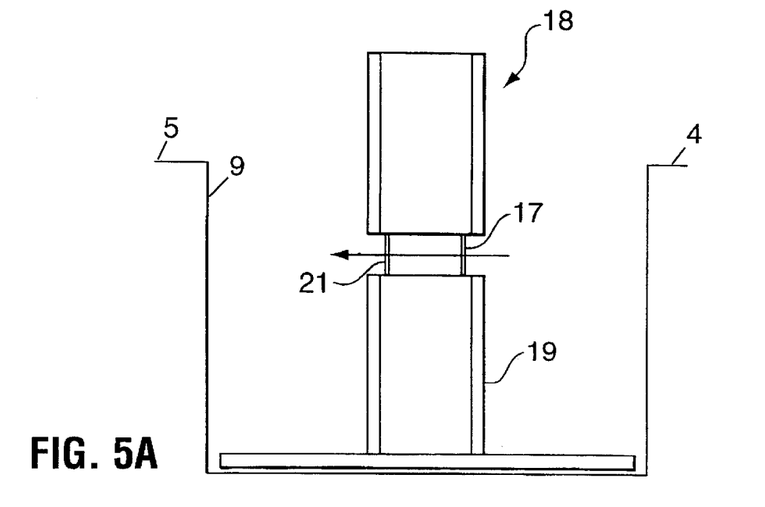
FIGS. 5A and 5B are front and side views of a sample holder mountable in the block of FIG. 5.
Figure 5B:
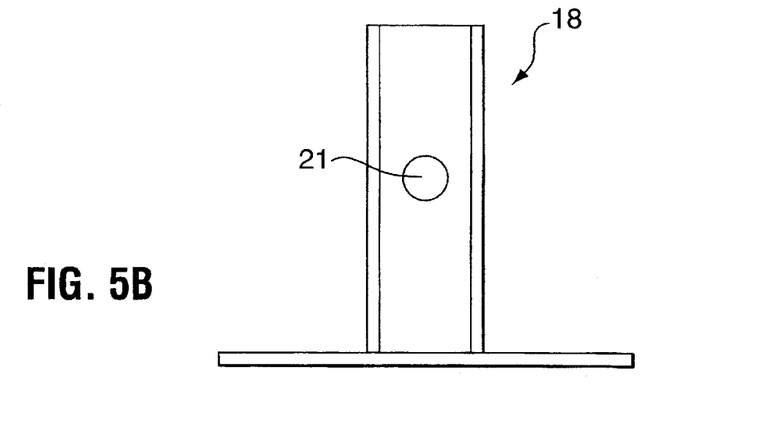
Figure 6:
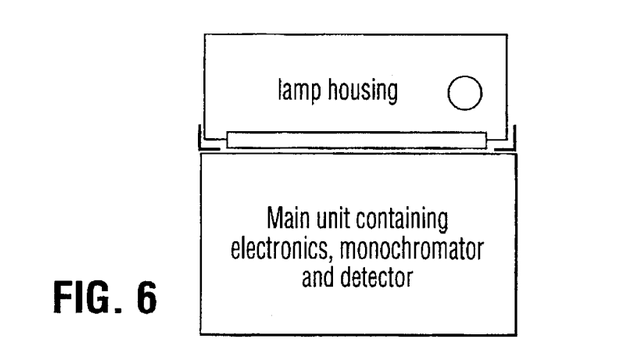
FIG. 6 is a front schematic view of the instrument of the present invention.

The sample holder block used in the LFP unit of the present invention is shown in FIGS. 5, 5A and 5B. It comprises a rigid block 1, preferably of aluminum or any other suitably inflexible material, having a central hollow space, as shown in FIG. 5, into which a sample container can be mounted. The sample container 18, comprises a square quartz tube or curette 17, as shown in FIG. 5A and 5B, and is placed in space 9, as shown in FIG. 5. The frame 19 of the sample holder is provided with apertures 20, 21 at right angles to one another for the laser and monitoring light, respectively. Space 9 is flanked by blocks 4, 5 each of which is provided with a central bore 7, 8. A slot 6 is provided in each block, for the placement of filters or the like, if desired. The laser shutter affixes to the breadboard adjacent the sample holder, using the grid of tapped holes.

Figure 4:
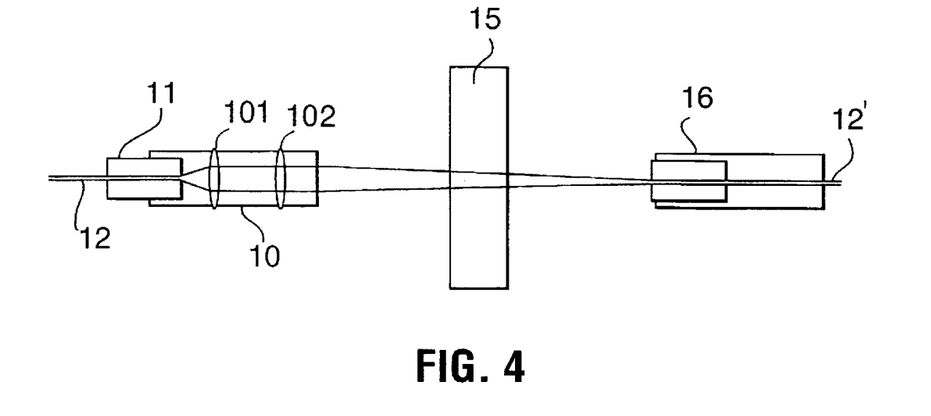
FIG. 4 is a schematic detail of the optical arrangement of the present invention.
Figure 7:
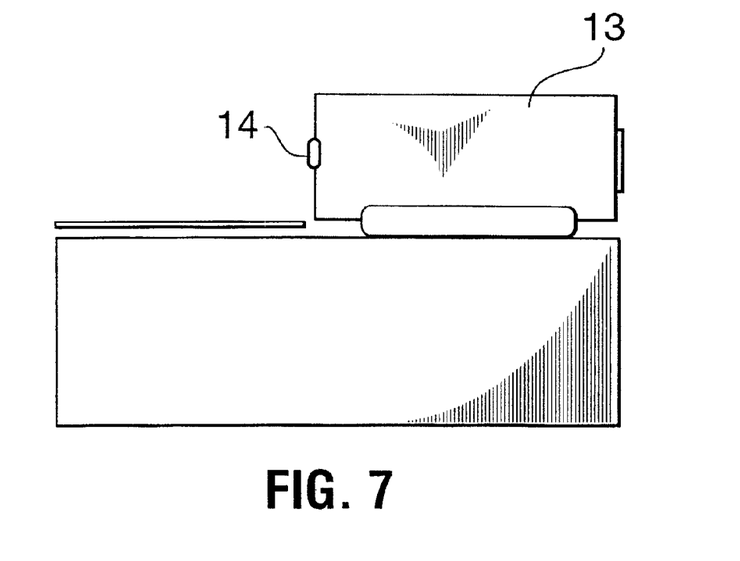
FIGS. 7 and 7A are side and side perspective schematic views of the instrument of the present invention.
Figure 7A:
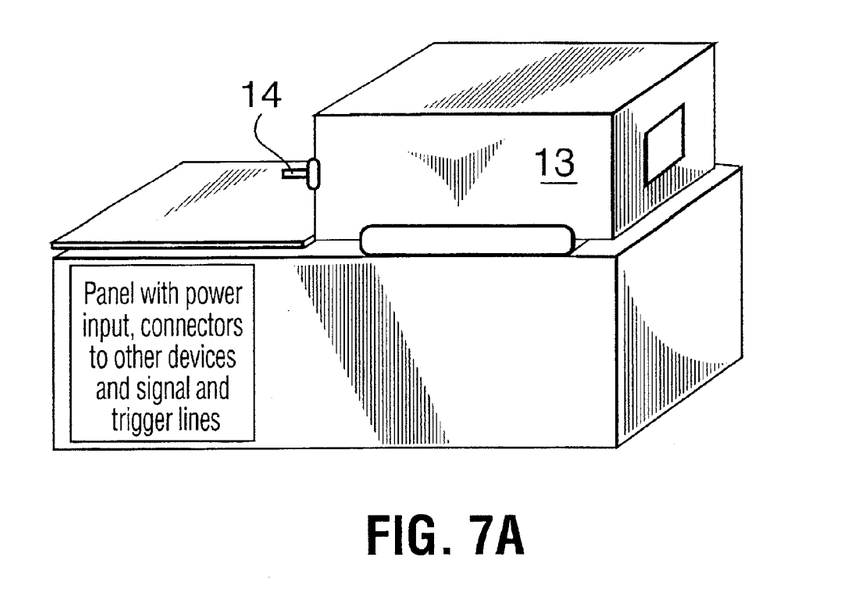
Figure 8:
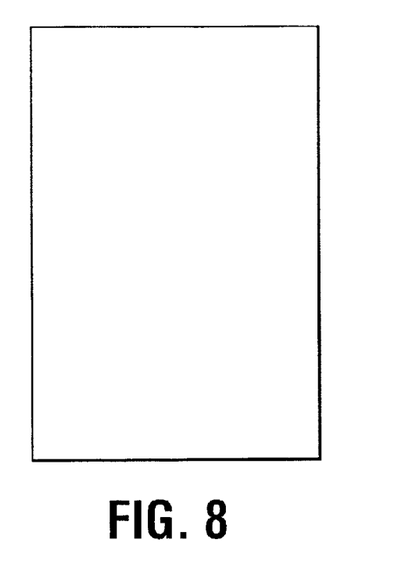
FIGS. 8 and 8A are top view of the base plate and top level plate of the instrument of the present invention.
Figure 8A:
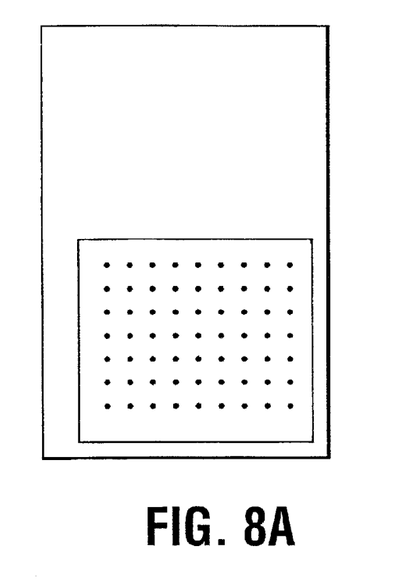

The bores 7, 8 in blocks 4, 5 are coaxially aligned. Referring to FIG. 4, a collimator 10 with fused silica lenses 101, 102 is mounted in bore 7 of block 4 of FIG. 5. The collimator 10 is affixed by a fibre adaptor 11 to a silica fibre 12, as shown in FIG. 4. The silica fibre 12 extends from lamp housing 13 which is provided with a suitable fibre connector 14, as shown in FIGS. 7 and 7A.

The fused silica lenses of the collimator forms the light from the lamp in housing 13 through the sample cell 15 to a beam pick up 16, mounted in the bore 8 of the opposite block 5.

Referring in more detail to FIG. 4, a fiber optic cable 12 (left) delivers light from a xenon lamp to a lens assembly. From left to right, the first lens (focal distance≦10 mm) collimates the beam, while the second lens (for example FL~50 mm) focuses the beam through the sample onto the fiber that delivers the signal to the monochromator-PMT assembly. The signal pick-up fiber on the right is slightly smaller than the size of the light spot from the lens assembly, thus allowing for some tolerance in the alignment of the system. Importantly, the sample compartment requires no lenses on the right side. This allows for excellent discrimination between the absorption signals needed for detection and the unwanted signals due to scattered light and fluorescence. This modality of discrimination is referred to as "solid angle-based signal discrimination" and the importance of this approach as compared to methods based on lamp-pulsing (which are conventionally used) is explained below.

As noted, the novel arrangement of FIG. 4 does not require a lens between the sample compartment and the tip of the fiber optic cable that transmits the light to the detection system. As a result, unwanted emissions (scattered light or fluorescence) which originate at the sample and propagate in all directions are not concentrated at all. Thus, the fraction of these emissions picked up by the small tip (typically 200 µm to 1000 µm) of the fiber is too small to cause interference with the actual signal. This allows outstanding discrimination. Key to this discrimination is he optical design shown in FIG. 4 to the left of the sample which captures the delivery fiber output and concentrated it through the sample (normally contained in a quartz curette) and on to the signal pick-up fiber 12'.

As can be seen in FIGS. 4 and 5, moreover, the sample holder, lens assembly, laser input and fiber optic pick up together form an assembly that may be detached from the remainder of an assembly, connected thereto only by fiber optic cables (and power cables). This provides the instrument of the present invention with flexibility of application impossible with prior art systems. For instance, the sample holder sub-assembly shown in FIGS. 4 and 5 could be used remotely from the bulkier part of the instrument, for instance in a hazardous environment or an industrial environment, to analyze for the presence, or absence of a substance in a product flow line.

Figure 3:
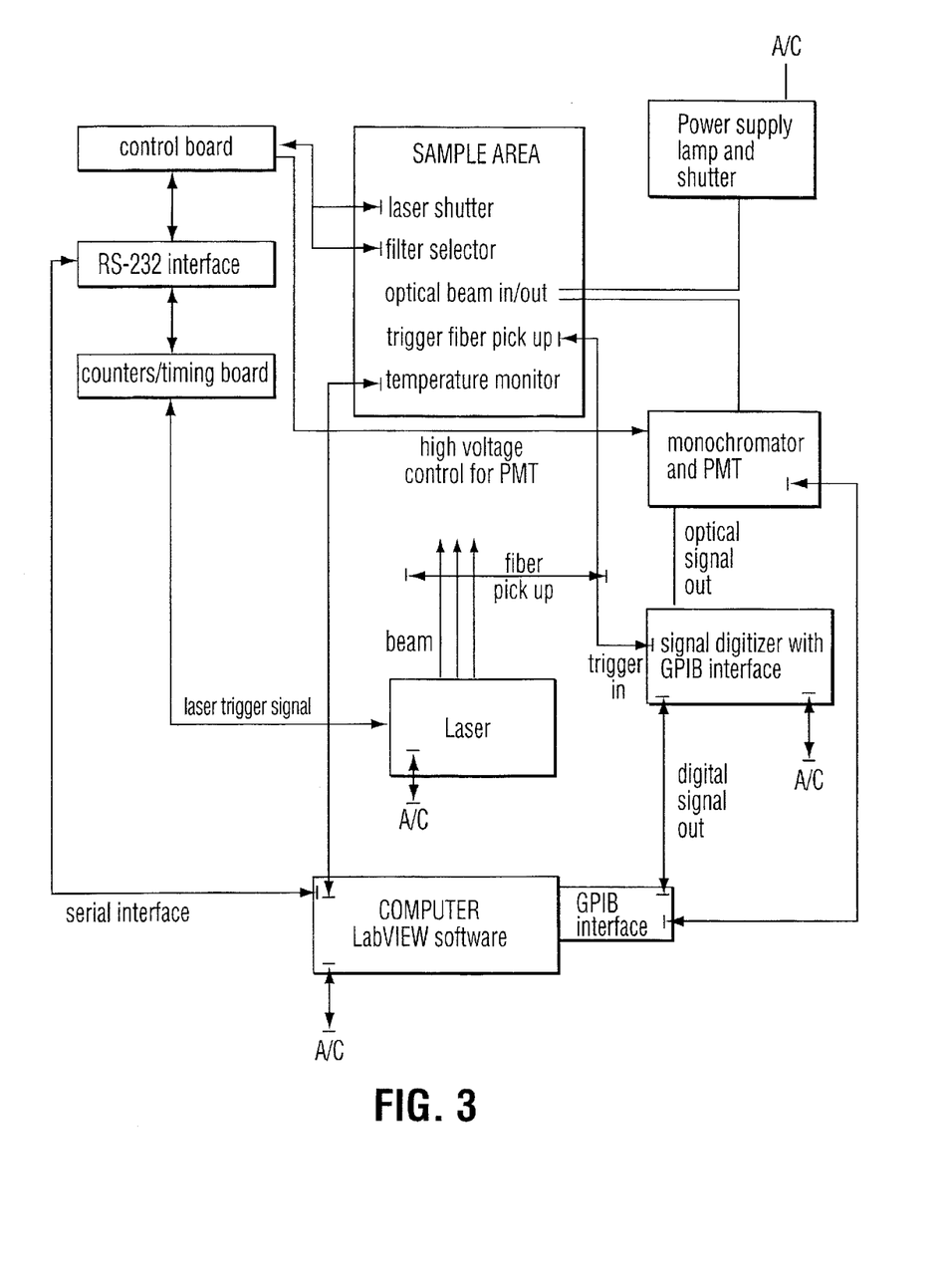
FIG. 3 is a schematic/block diagram of the outline of main component connectivity of the flash photolysis system of the present invention.

The overall component connectively of the LFP instrument of the present invention is illustrated in FIG. 3.

Traditionally, scattered light and sample or component fluorescence have been a problem in LFP techniques. The origin of this problem relates to the high peak power of the laser compared to the power of conventional lamps. For example, the monitoring beam in a LFP system may use a Xenon lamp of 50 to 1000 watt rating; only a small fraction of this power results in light output actually used by the LFP system. In contrast a typical modem pulsed laser will have peak powers in the 10 megawatt range. Thus, even if a small fraction of this power is either scattered or converts to fluorescence emission, its intensity may greatly exceed that reaching the sample from the monitoring lamp. Traditionally, the monitoring lamp (usually a Xenon lamp) had been pulsed for a few milliseconds; that is its intensity has been increased by discharging a bank of capacitors so as to increase the lamp intensity by a factor between 2 and 100. This increases the monitoring beam intensity without enhancing the fluorescence or scattered light. Lamp pulsing thus helps signal discrimination; it also helps capture the fast response from the PMT required in this work. In traditional LFP, one or more lenses located between the sample and the monochromator concentrate the signal on the monochromator slit. These lenses also concentrate on the detection system any unwanted fluorescence or scattered light.

While lamp pulsing, as explained before has been the preference of most practitioners of the LFP technique, it places severe limitations on the use of the technique in time scales exceeding 1 millisecond. Under normal circumstances the relatively inefficient collection of light from the monitoring lamp source then leads to some limitations in the quality of the data captured. In particular, increase in the number of PMT dynods used, or on the load resistor used at the detection end leads to reduced capabilities when capturing fast signals, particularly in the 1 ns to 100 ns range. The reduced ability to discriminate against sample emission (fluorescence, scattering and Raman components) affects the quality of measurements in a wide range of time scales, but the problem is most acute in short time scales, with absorption signals being frequently preceded by a negative spike reflecting undesirable emissions.

Many combinations of commercially available components can be used to assemble the mLFP system described here. However, we have made a selection that works well in combination with each other, leading to excellent results in terms of signal-to-noise and allows the miniaturization and portabiltiy desired to be achieved. Further, this combination offers a cost effective solution. The following key components lead to a system with group operating characteristics:

(a) The integrated lamp-power supply unit is from ILC Technologies, model CXE-175 with lamp EX-175-10, UV Xenon lamp.

(b) The monochromator is model CM-110 from CVL. The unit is described as a 1/8meter model. Several gratings can be used such as grating #DK 121230 with a range from 200 to 750 nm.

(c) The detector incorporates a miniature PMT from Manamatsu, model R5600U-04, with response in the 185 to 820 nm region. It has been wired to use all but one amplification stage in the dynod chain. The number of dynods used can be changed to accommodate user need.

(d) The PMT is powered by a power supply module from Spellman, model MPI-N. This programmable unit is controlled by feedback circuitry from the PMT to provide an output level requested by the computer via interfaces designed specifically for mLFP control.

(e) The oscilloscope/digitizer that captures the data and transmits it to the computer is a Tektronix unit, model TDS-3032 with 300 MHz response and a GPIB interface model TDS-3GM.

(f) The control software is written in the LabView language from National Instruments. Version 4 for Windows was employed (Part 776678-03), although other versions, or versions for other platforms (e.g., Macintosh), could also be employed.

(g) The computer is a Pentium II computer with a GPIB interface from National Instruments, part #777073-51.

(h) A number of minor components add functionality to the system, such as a temperature monitor and a pick-up fiber optic cable that detects the laser pulse.

It will be understood that the instrument described herein is susceptible of numerous modifications and developments, including:

i) A lens at the bottom of the sample compartment to bias the system in favor of fluorescence, thus allowing the pick-up of emission signals with a fiber to detect spectra and time evolution of fluorescence and phosphorescence signals.

ii) A near-IR detector can be placed at the bottom of the sample compartment in order to detect emission in this region. Specifically this will be useful to monitor singlet oxygen (a high energy form of oxygen that emits phosphorescence).

iii) Recent development in CCD and fiber technologies will allow the addition of a commercial grating and CCD detector to add functionality as a "normal" UV-visible spectrometer (i.e., not coupled with a laser) capable of response in longer time scales (0.1 seconds and up).

iv) A MLFP spectrometer capable of response at 320 nm and longer wavelengths (the UVA model) can be built around less expensive lamps and components.

It has a slower response, starting at about 100 ns, but is economical to construct. Such a unit may be used in teaching and in some biological areas.

EXAMPLES

A number of preliminary experiments have demonstrated the capabilities of the system of the present invention. Representative ones follow:

Example 1

Figure 9:
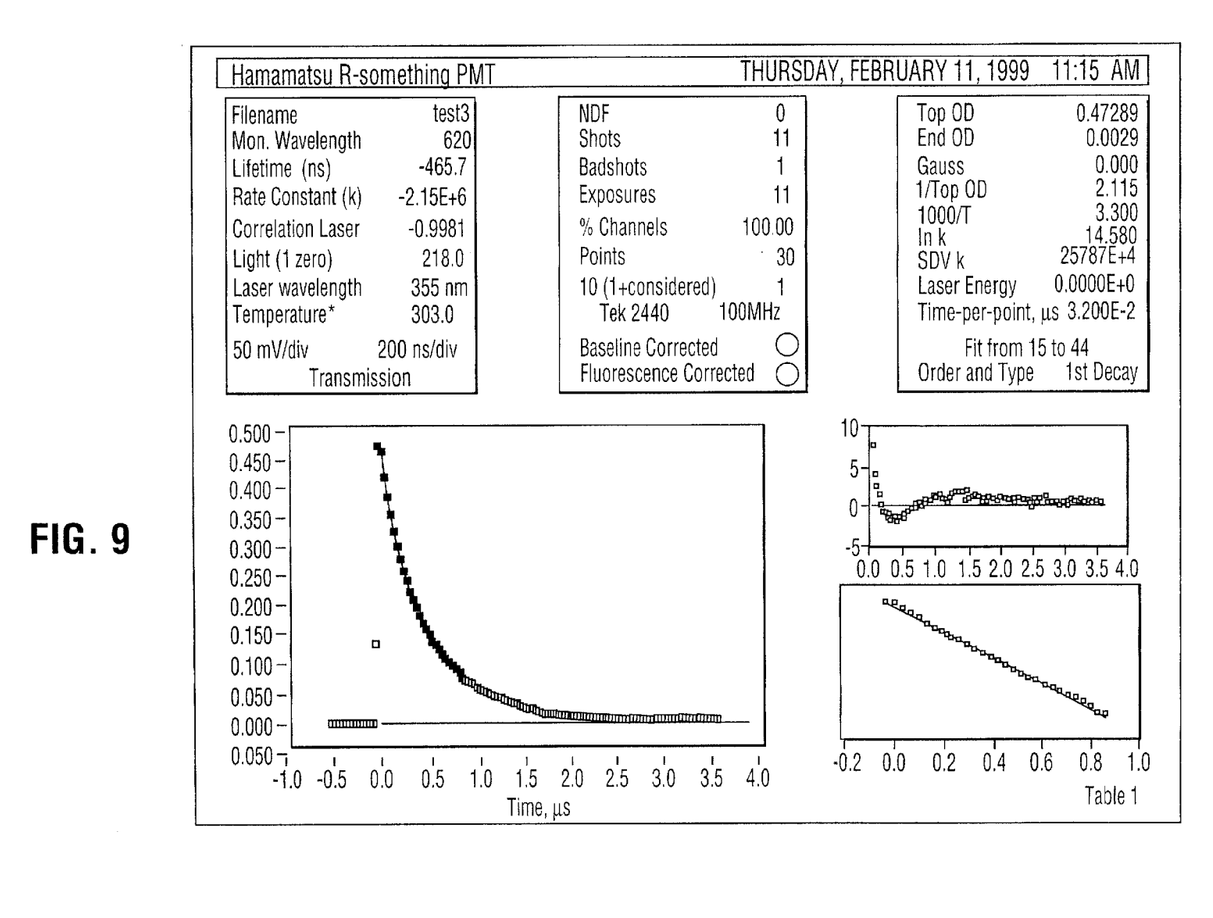
FIG. 9 is a graph illustrating the absorption signal obtained from a sample of xanthone excited at 355 nm with the third harmonic from a Nd/YAG laser.
Figure 9A:
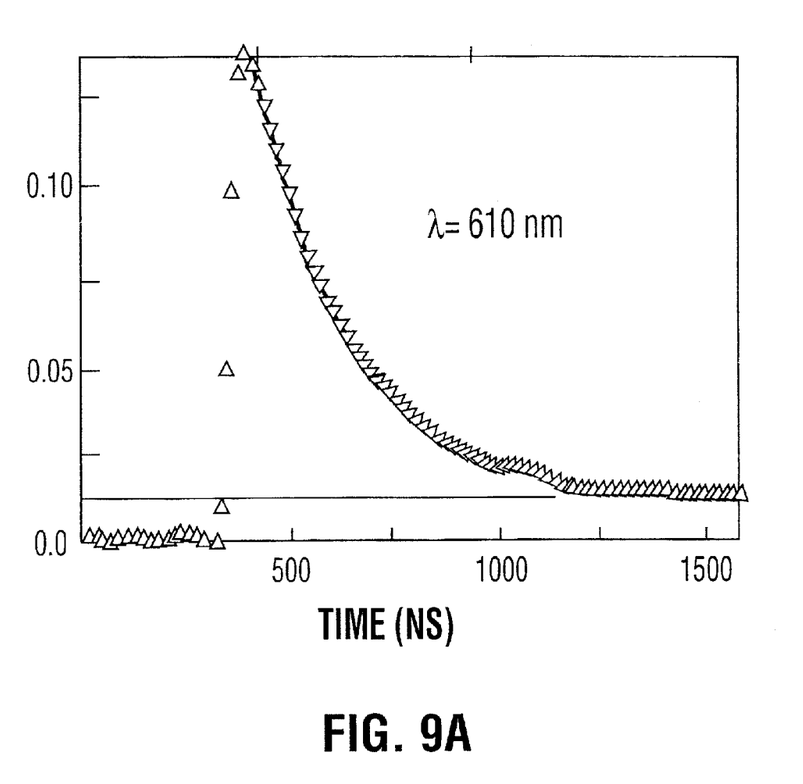
FIG. 9A is a comparative graph, from "Solvent Effects in the Photochemistry of Xanthone" J C Sciano, J.Am. Chem. Soc., Vol.102, No. 26, 1980, illustrating an absorption spectrum of xanthone, utilizing conventional techniques.

Referring to FIG. 9, Crystalline xanthone from Aldrich was dissolved in methanol, such that its optical absorption in a spectrometer cell with a 7 mm optical path would be 0.30. 2 mL of this solution were placed in a cell constructed of 7 mm×7 mm square quartz tubing, terminated at the top with 4 inches of round quartz tubing of approximately 7 mm internal diameter. This tube was capped with a rubber septum that allowed the sample to be deaerated by bubbling highly purified nitrogen. Nitrogen bubbling eliminates oxygen that acts as a triplet state quencher and thus reduces the triplet lifetime. Bubbling was continued for about 15 minutes, that is adequate to eliminate most (>99%) of the oxygen from the cell. This sample was then utilized for alaser experiment, that consisted in the exitation at 90 degrees (with respect to the monitoring beam) with the 355 nm pulses from the third harmonic of a Surelite Nd/YAG laser from Continuum. The main plot in the figure illustrates the evolution of the absorbance signal recorded at 620 nm with time, with the time expressed in microseconds. The laser pulse reaches the sample at the point of sudden absorbance increase, i.e. at about 0.0 microseconds. The vertical axis displays units of change in absorbance for a 7 mm optical path. The signal observed is due to the excited triplet of xanthone and is a well charecterized species. It is based on the average data collected during 11 laser shots. A contrasting example from the prior art is shown in FIG. 9A.

Example 2

Figure 10:
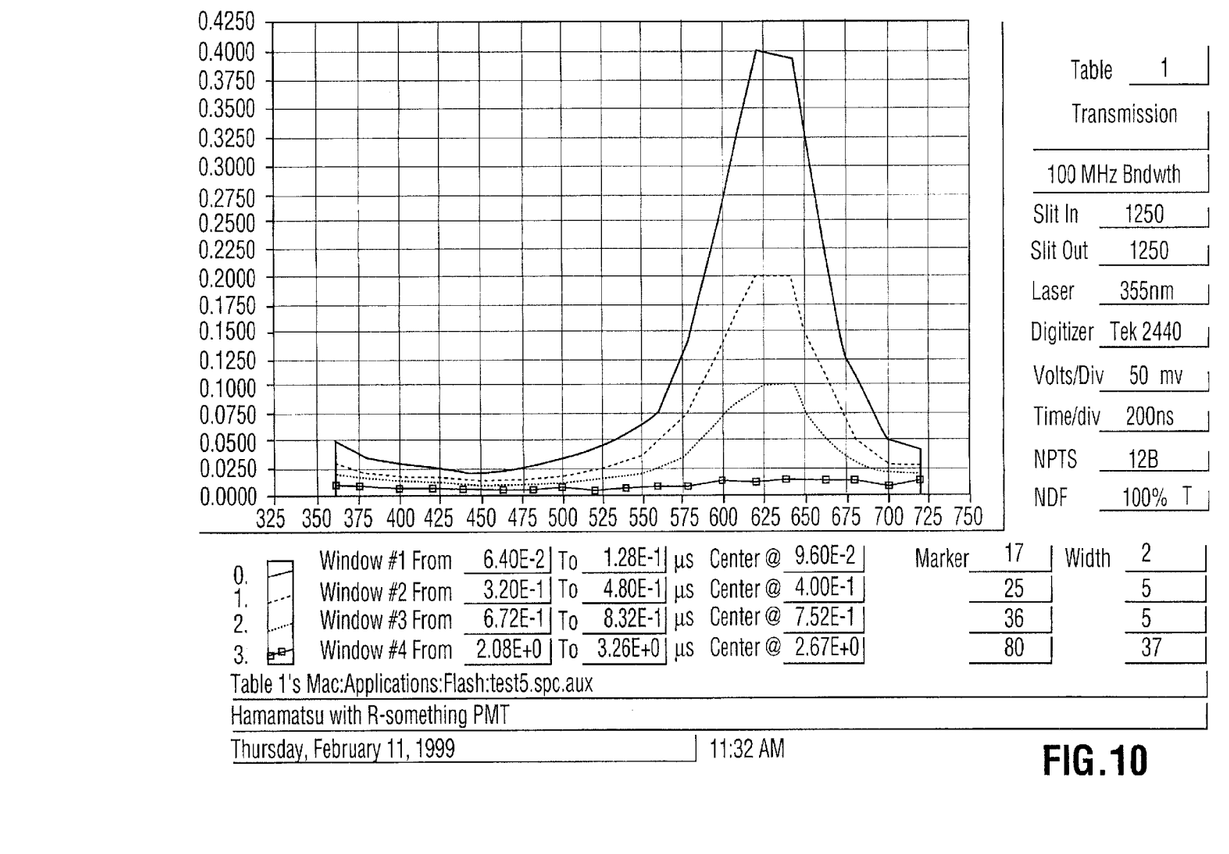
FIG. 10 is the transient spectrum of the sample of FIG. 9.

FIG. 10 shows the spectrum of triplet xanthone captured during its decay in the same sample of FIG. 9. A number of traces, such as that of FIG. 9 were collected at different monitoring wavelengths. For each of the traces the absorbance was read at the times indicated at the bottom of FIG. 10 under the heading "Center @", which provides this information in units of microseconds. Repetition of the experiment (under automatic control) allows the operator to construct the spectra of FIG. 10, recorded at the 4 different times indicated in "Center @". The weakening of the signal with time is a reflection of the same decay already illustrated in FIG. 9. Practitioners of the art will readily recognize the spectra of FIG. 10 as that of triplet xanthone.

Example 3

Figure 11:
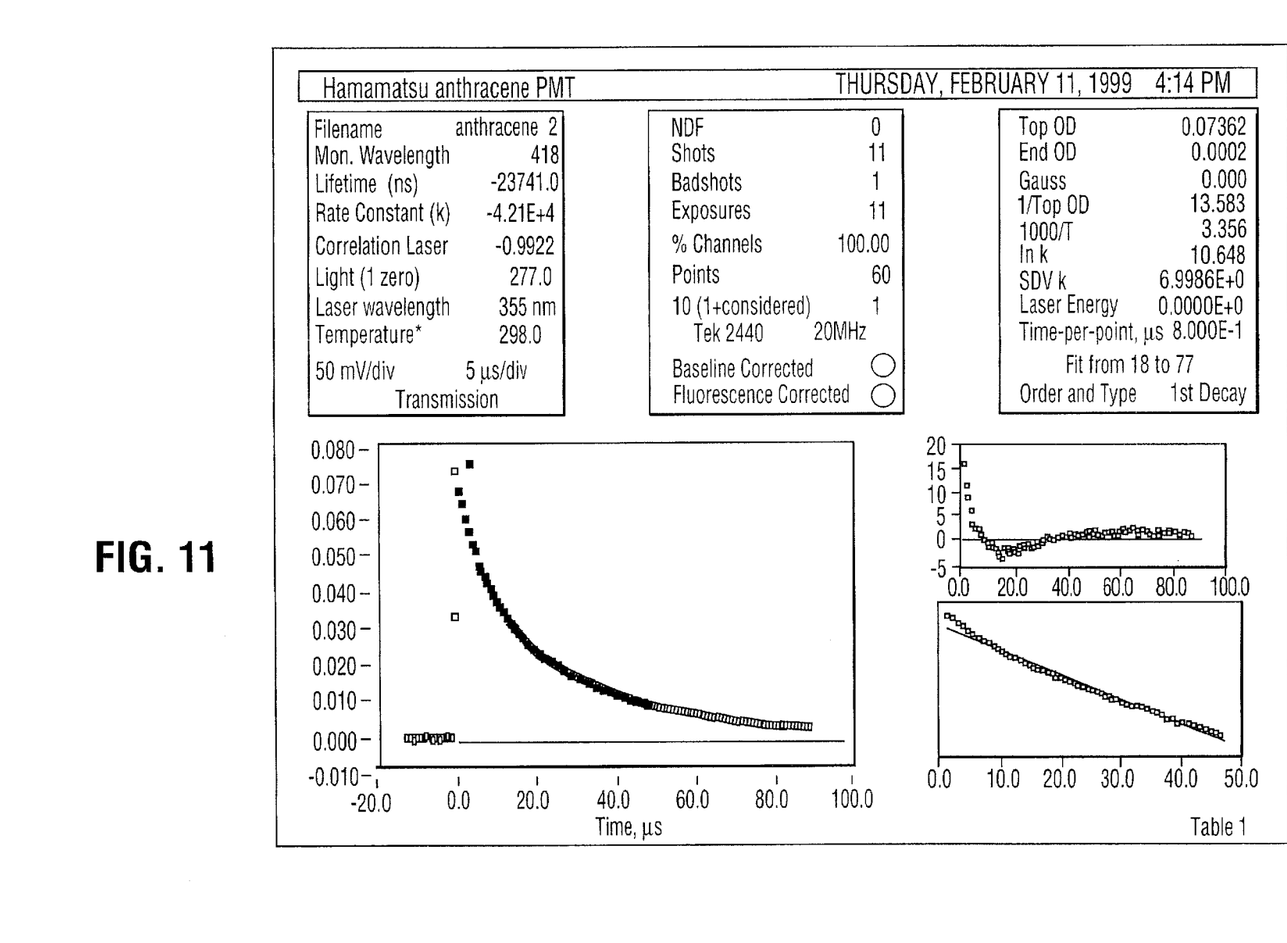
FIG. 11 illustrates the absorption signal obtained from a sample of anthracene excited at 355 nm.

A sample of anthracene was prepared in the same cell and following the same protocol indicated for xanthone in the case of Example 1. The signal observed following 355 nm later excitation is that of the excited triplet state of anthracene, and is shown in FIG. 11.

Example 4

Figure 12:
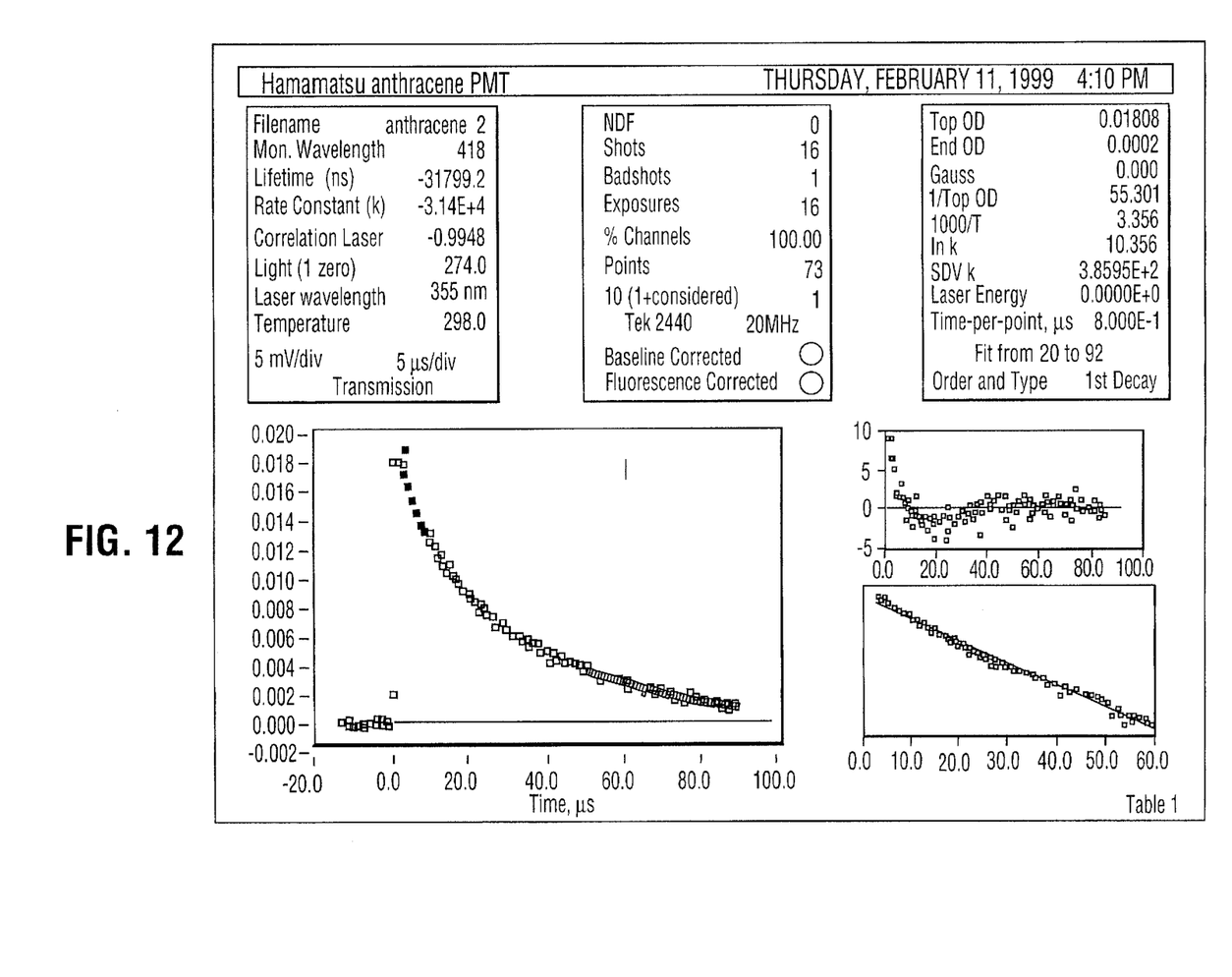
FIG. 12 illustrates the sample of FIG. 11, attenuated by the use of neural optical filters by about a factor of 4.

The sample of example 3, with the signal attenuated by use of neutral optical filters by about a factor of 4. Signal quality remains excellent (FIG. 12). The signal decay is now slower due to reduced importance of a process known as triplet-triplet annihilation.

It is to be understood that the examples described above are not meant to limit the scope of the present invention. It is expected that numerous variants will be obvious to the person skilled in the field of analytical chemistry without any departure from the spirit of the invention. The appended claims, properly construed, form the only limitation upon the scope of the invention.

The Embodiments of the Invention in Which Exclusive Property or Privilege is Claimed are Defined as Follows:

1. Apparatus for flash photolysis including:
   i) a source of light radiation;
   ii) optical means for channeling light for said source through a sample;
   iii) means to initiate a chemical change in said sample;
   iv) means for measuring the change in absorption of said light radiation by said sample during said chemical changes in absorption of said light radiation by said sample during said chemical change; and wherein said optical means includes a first optical fibre from said source of light radiation to said sample and a second optical fibre from said sample to said means for measuring, said optical means further including a first lens to focus light from said first optical fibre, through said sample to said second optical fibre.

2. Apparatus as claimed in claim 1, wherein said means for initiating a chemical change (iii) comprises a laser arranged to emit a beam of light onto said sample.

3. Apparatus as claimed in claim 1, wherein said optical means includes a first lens to focus light from said first optical fibre, through said sample to said second optical fibre.

4. Apparatus as claimed in claim 3, further including a sample holder positioned between said first lense and said second optical fibre.

5. Apparatus as claimed in claim 4, wherein said laser is optically connected to said apparatus adjacent said sample holder by a third optical fibre.

6. Apparatus as claimed in claim 5, wherein said first, second and third optical fibers terminate in a portable assembly including said sample holder and said lenses.

7. Apparatus as claimed in claim 1, arranged in a portable assembly.

8. Apparatus as claimed in claim 1, arranged in a bench top housing.

9. Apparatus as claimed in claim 2, wherein said optical means includes a first lens to focus light from said first optical fibre, through said sample to said second optical fibre.

10. Apparatus as in claim 4, further including a sample holder positioned between said first lense and said second optical fibre.

* * * * *